United States Patent [19]

Tanaka et al.

[11] Patent Number: 4,762,605
[45] Date of Patent: Aug. 9, 1988

[54] OXYGEN SENSOR

[75] Inventors: Takeo Tanaka; Keisuke Sugimoto; Yuji Sugiyama; Hideo Shiraishi; Teizo Takahama; Masahiko Masuda, all of Kanagawa, Japan

[73] Assignee: Fuji Electric Co., Ltd., Kanagawa, Japan

[21] Appl. No.: 8,655

[22] Filed: Jan. 30, 1987

[30] Foreign Application Priority Data

| Feb. 1, 1986 | [JP] | Japan | 61-13495[U] |
| Feb. 1, 1986 | [JP] | Japan | 61-13496[U] |
| Mar. 5, 1986 | [JP] | Japan | 61-47512 |
| Jun. 3, 1986 | [JP] | Japan | 61-128747 |
| Jun. 13, 1986 | [JP] | Japan | 61-89387[U] |
| Jul. 24, 1986 | [JP] | Japan | 61-174088 |

[51] Int. Cl.⁴ ............................................. G01N 27/58
[52] U.S. Cl. ..................................... 204/406; 204/410; 204/425
[58] Field of Search ................. 204/425, 406, 1 S, 410

[56] References Cited

U.S. PATENT DOCUMENTS

| 3,514,377 | 5/1970 | Spacil et al. | 204/425 |
| 4,547,281 | 10/1985 | Wang et al. | 204/424 |
| 4,601,809 | 7/1986 | Kitahara | 204/406 |

FOREIGN PATENT DOCUMENTS

| 52-69690 | 1/1977 | Japan | 204/425 |
| 31419/1980 | 6/1980 | Japan | 204/425 |

Primary Examiner—G. L. Kaplan
Attorney, Agent, or Firm—Finnegan, Henderson, Farabow, Garrett & Dunner

[57] ABSTRACT

A limited current type oxygen sensor comprises a solid electrolyte element formed from material having high oxygen-ion conductivity such as yittria-stabilized zirconia. Electrodes are provided on the top surface and the bottom surface of the element and are formed by calcining a mixture of small ceramic particles that are relatively sinter-retardant as compared with oxygen-ion conducting ceramics, of 200 Å in average particle size fine precious metal particles, and a binder. A cover is provided over the second electrode and the cover includes at least one diffusion orifice that permits ambient gas to diffuse toward the second electrode. The dry-gas-based and humid-gas-based oxygen content of the gas is determined by applying a first voltage less than the theoretical water decomposition voltage and a second voltage greater than the theoretical water decomposition voltage to the electrodes to generate corresponding currents associated with the oxygen-ions which flow through the electrolyte element between the first electrode and the second electrode. A heater may be buried in the electrolyte element to increase the flow rate of oxygen ions between the electrodes.

14 Claims, 9 Drawing Sheets

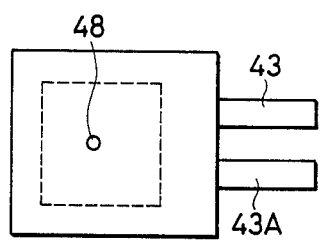
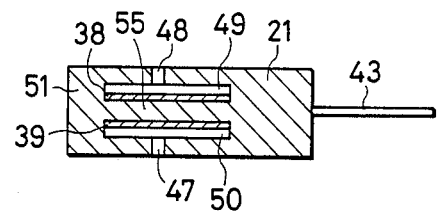
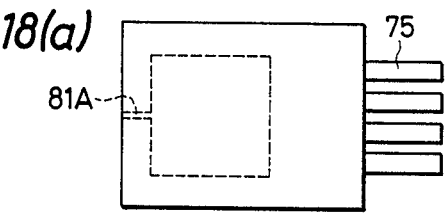
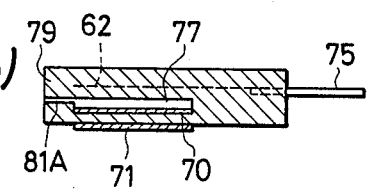
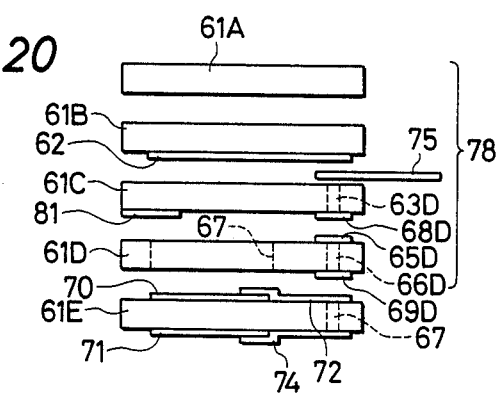

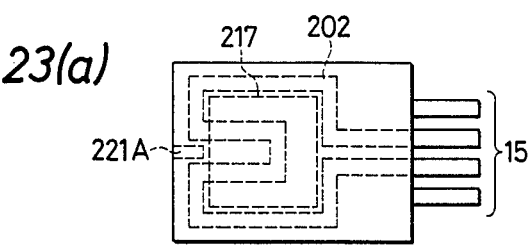
FIG. 23(a)
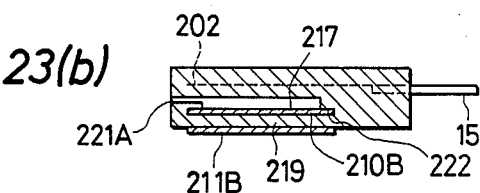
FIG. 23(b)
FIG. 24
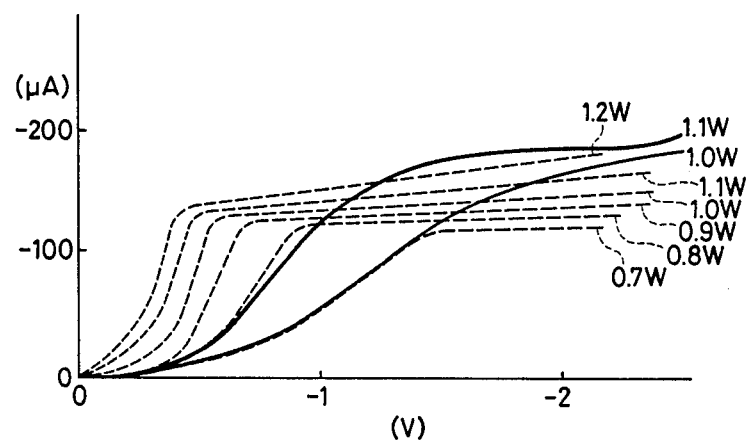

OXYGEN SENSOR

FIELD OF THE INVENTION

This invention relates to an oxygen sensor capable of detecting dry-gas-based oxygen content rendered unaffected by water vapor by making use of the oxygen ion conductivity of stabilized zirconia at high temperatures and the electrolysis of the water vapor at the electrodes.

BACKGROUND OF THE INVENTION

FIG. 1 is an illustration of the principle of operation of a zirconia oxygen sensor, wherein a zirconia ceramic element 1 that is stablized with yttria ($Y_2O_3$) or calcia (CaO) and is heated to high temperatures to form a solid electrolyte with only mobile oxygen ions. Catalytic electrodes 2 of platinum are formed on both sides of the stabilized zirconia element 1 and a voltage V is applied across the electrodes 2. In contact with one of the electrodes 2 which is biased to the lower potential, oxygen is converted into $O^2$ ions. Current flows through the stabilized zirconia element 1 and the oxygen content can be determined from the current level.

FIG. 2 is an illustration of a limited current type oxygen sensor using the stabilized zirconia element 1. As shown in FIG. 2, a minute diffusion orifice 4 is provided with a cover 3. Dry-gas-based oxygen content excluding water vapor is normally required to determine oxygen content and this makes it necessary to supply gas being examined without water vapor content separately for correction purposes. The above methods are disadvantageous in that they require complicated arrangements and make the measuring process tedious and complicated.

OBJECTS AND SUMMARY OF THE INVENTION

The present invention is intended to effectively solve the above problems inherent in the prior art and it is therefore an object of the present invention to provide an oxygen sensor which is compact, easy to operate and simple in construction.

Another object of the present invention is to shorten the process of producing a limited current type oxygen sensor using oxygen-ion conducting ceramics by sintering the oxygen-ion conducting ceramics and forming electrodes simultaneously.

It is still another object of the present invention to provide a reliable oxygen sensor excellent in thermal efficiency.

These and other objects are attained by a limited current type oxygen sensor comprising an oxygen-ion conducting solid electrolyte element, said element having a top surface and a bottom surface, a first electrode on the bottom surface, a second electrode on the top surface; means for covering the second electrode, the covering means including at least one diffusion orifice permitting ambient gas to diffuse therethrough toward the second electrode, means for alternately applying a first voltage to one of the electrodes and for measuring the level of a first current flowing through the element between the first electrode and the second electrode responsive to the application of the first voltage and a second voltage different from the first voltage to the one electrode and for measuring the level of a second current flowing through the element between the first electrode and the second electrode responsive to the application of the second voltage, the first voltage having a level less than the theoretical water decomposition voltage such that the first current is related to the decomposition of oxygen on the second electrode and the second voltage having a level greater than the theoretical water decomposition voltage such that the second current is related to the decomposition of oxygen and decomposition of water vapor in the space, and operational circuit means receiving the first current and the second current and for determining therefrom the dry-gas-based and humid-gas-based oxygen content of the ambient gas.

In another embodiment of the invention, the limited current type oxygen sensor comprises an oxygen-ion conducting solid electrolyte element, the element having a top portion and a bottom portion, the top portion having a bottom surface and the bottom portion having a top surface in opposition to the bottom surface of the top portion and a bottom surface, a portion of the bottom surface of the top portion being separated from the top surface of the bottom portion to define a space therebetween, the element including a diffusion orifice permitting ambient gas to enter the space, a first electrode formed on the bottom surface of the bottom portion, a second electrode on the top surface of the bottom portion, a portion of the second electrode communicating with the space, a heater buried in the top portion of the element, means for supplying current to the heater to generate heat for heating the space, means for alternately applying a first voltage to one of the electrodes and for measuring the level of a first current flowing through the bottom portion of the element between the first electrode and the second electrode responsive to the application of the first voltage and a second voltage different from the first voltage to the one electrode and for measuring the level of a second current flowing through the element between the first electrode and the second electrode responsive to the application of the second voltage, the first voltage having a level less than the theoretical water decomposition voltage such that the first current is related to the decomposition of oxygen in the space and the second voltage having a level greater than the theoretical water decomposition voltage such that the second current is related to the decomposition of oxygen and water vapor in the space, and operational circuit means receiving the first current and the second current for determining therefrom the dry-gas-based and humid-gas-based oxygen content of the ambient gas.

As a further aspect of the present invention, a process for producing a limited current type oxygen sensor comprises the steps of forming a sintered oxygen-ion conducting solid electrolyte element, forming a first electrode on the bottom surface of the element and a second electrode on the top surface of the element by calcining a mixture of small ceramic particles of 600 Å to 900 Å in particle size, relatively sinter-retardant when compared with oxygen-ion conducting ceramics of 200 Å in average particle size, fine precious metal particles and of 100 Å to 200 Å in particle size a binder, covering the second electrode to define a space above a portion of the second electrode and to form a diffusion orifice permitting ambient gas to enter the space, providing means for applying selected voltage levels to one of the electrodes to cause corresponding currents to flow through the element between the first electrode and the second electrode such that the levels of the currents indicate the oxygen content of the gas in the space, and providing operational circuit means for determining the dry-gas-based and humid-gas-based oxygen content of the gas from the currents flowing through the element.

BRIEF DESCRIPTION OF THE DRAWINGS

The manner by which the above objects and other objects, features and advantages of the present invention are attained will be fully apparent when the following detailed description is considered in view of the accompanying drawings, wherein:

FIGS. 17 (a) and (b) are a top view and a sectional view, respectively, of an oxygen sensor with vacancies according to the present invention;

FIGS. 18 (a) and (b) are a top view and a sectional view, respectively, of a fourth embodiment of an oxygen sensor according to the present invention;

FIG. 20 is a side view showing a laminate of the first, second, third, fourth and fifth green sheets according to the embodiment of FIGS. 18 (a) and (b);

FIGS. 23 (a) and (b) are a top view and sectional view, respectively, of a fifth embodiment of the oxygen sensor of the present invention;

FIG. 24 shows electric characteristics of the oxygen sensor of FIGS. 23(a) and (b);

DETAILED DESCRIPTION

Figure 3:
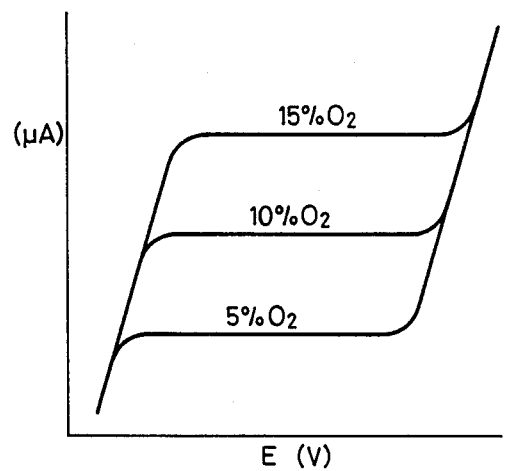
FIG. 3 is a graph showing the plateau characteristics of the limited current in the sensor of FIG. 2.
Figure 4:
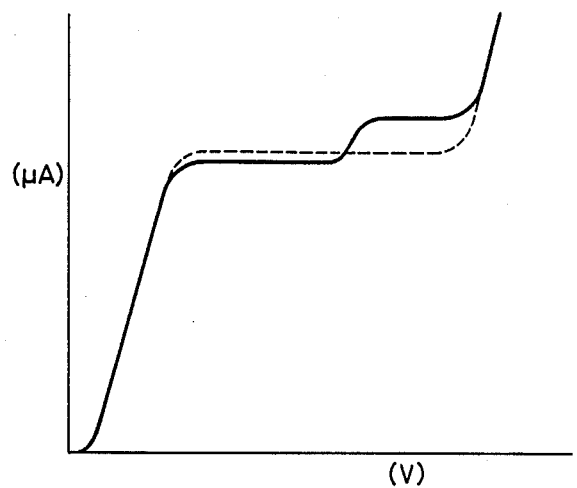
FIG. 4 is a graph showing the theoretical plateau characteristics having a two-stage plateau zone according to the present invention.

As a result of studies and experiments carried out by the present inventors, it has been found that a two-stage plateau zone as shown in FIG. 4 appeared when the voltage applied to the electrodes 2 was raised in a gaseous atmosphere containing water vapor. This phenomenon has been found to be accompanied with the electrolysis of water vapor at the electrode 2 resulting from application of voltage greater than the theoretical water decomposition voltage (of about 1.23 V) and great enough to compensate for voltage drop at the electrode 2. Accordingly, the present inventors arrived at a conclusion that, by changing the voltage applied, dry-gas-based or humid-gas-based oxygen content could be measured and simultaneously a water vapor content (absolute humidity) signal could be obtained by subtracting the oxygen content from the measured value of the dry-gas-based or humid-gas-based oxygen content. What is shown by a dotted line signifies a plateau zone in the dry gas in contradistinction to the characteristics shown in FIG. 3.

The oxygen sensor of the present invention is characterized in that a first voltage smaller than the theoretical water decomposition voltage and a second voltage greater than the theoretical water decomposition voltage are switched on or off and alternately applied across electrodes therein so that the limited current may solely rely on oxygen in the case of the latter and that an operational circuit is provided for holding and computing the first or second voltage to detect dry-gas-based or dry-gas-based and humid-gas-based oxygen content.

The present invention is intended to form electrodes offering excellent electrochemical properties by calcining fine precious metal particles of 100 Å to 200 Å in particle size mixed with small ceramic particles of 600 Å to 900 Å in particle size relatively sinter-retardant compared fine oxygen-ion conducting ceramics of 200 Å in average particle size to provide porous electrodes that do not sinter even at temperatures where fine oxygen-ion conducting ceramics sinter because of the sinter-preventative effect of the sinter-retardant small ceramic grains. Sintering of the precious metal grains is prevented by the sinter-preventive action of the sinter-retardant small ceramic grains.

The present invention is designed to provide a limited current type oxygen sensor comprising an oxygen-ion conducting solid electrolyte thin plate sandwiched between a cathode and an anode, a cover installed above the cathode to form an enclosed space, the cover being provided with an oxygen diffusion orifice communicating with the space, and a heater for heating the sensor.

The cover is incorporated with the thin plate by means of the oxygen-ion conducting solid electrolyte and the heater is buried in the oxygen-ion conducting solid electrolyte.

In other words, the cover is incorporated with the thin plate through the oxygen-ion conducting solid electrolyte to remove discontinuity at the boundary therebetween in order to prevent damage caused by the difference in thermal expansion coefficients between different materials. The heater is thermally coupled directly to the cathode, the anode and a portion of the solid electrolyte thin plate sandwiched between the electrode by burying the heater in the oxygen-ion conducting electrolyte which prevents the heat thus generated from being scattered and lost. Moreover, the construction of the present invention prevents the heater from evaporating because it is buried in the oxygen-ion conducting solid electrolyte.

Figure 1:
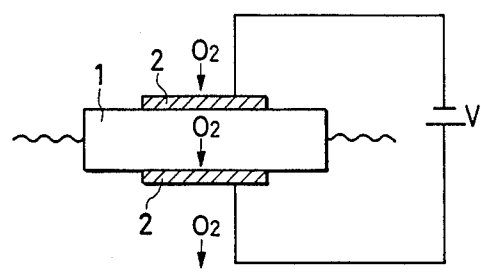
FIG. 1 is an illustration of a zirconia oxygen sensor.
Figure 2:
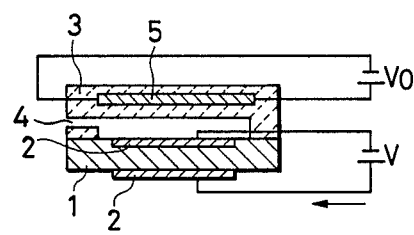
FIG. 2 is an illustration of a limited current type oxygen sensor.
Figure 5:
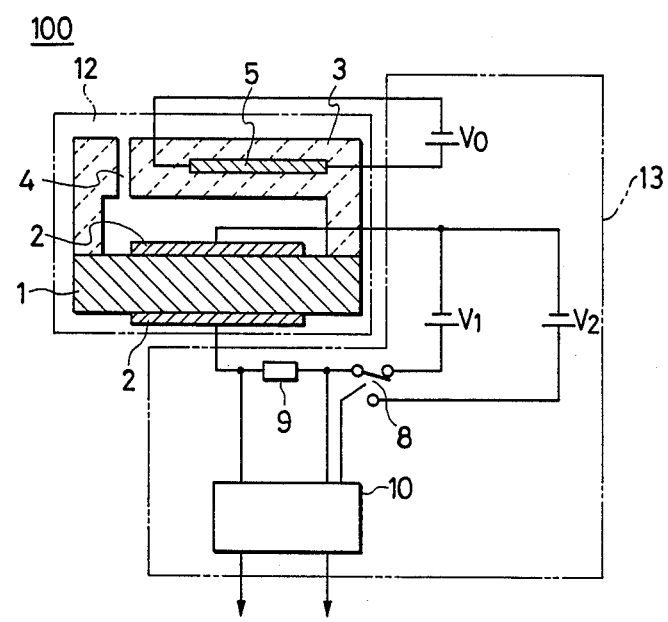
FIG. 5 is a schematic structural view of a first embodiment of the sensor of the present invention.

FIG. 5 is a schematic structural view of a first embodiment of the present invention, wherein like reference characters designate parts having functions similar to those shown in FIG. 2. An oxygen sensor 100 comprises a sensor means 12 and an electronic circuit 13. The sensor means 12 is provided with a stabilized zirconia element 1 sandwiched between two electrodes 2. One of the electrodes 2 is provided with a cover 3 having a minute diffusion orifice 4 and a heater 5 contained therein.

The electronic circuit 13 is equipped with a power supply switching circuit 8 for alternatively switching and supplying first and second voltages $V_1$, $V_2$ to the electrodes 2, an output resistor 9 for converting the output current of the sensors means 12 into a voltage, and an operational circuit 10 for holding and computing the level of the output signal through the output resistor 9. The voltage $V_0$ is used to operate the heater 5.

In the oxygen sensor thus constructed, the voltage $V_0$ preferably operates the heater 5 in the range of about 400°–900° C. so that the stabilized zirconia 1 may become an oxygen-ion conducting solid electrolyte, whereas the first voltage $V_1$ is selected to cause the limited current to rely on the oxygen content only. Moreover, the second voltage $V_2$ is selected to allow the electrolysis of water vapor and the decomposition of oxygen. The voltages $V_1$, $V_2$ are alternately applied to the electrodes 2 through the power supply computed by the operational circuit 10 to obtain a dry-gas-based oxygen output $\theta D$ from the following equation (1)

$$\theta D = AD \cdot H_1/100 - K(H_2 - H_1) \quad (1)$$

where $H_1$ = value of the output signal when the first voltage $V_1$ relies on the oxygen content; $H_2$ = value of the output signal when the second voltage $V_2$ relies on oxygen and water vapor; K = coefficient for the conversion of water vapor content; and AD = output-span correcting coefficient.

Subsequently, a humid-gas-based oxygen output $\theta W$ is computed by means of the following equation (2)

$$\theta W = AW \cdot H_1 \quad (2)$$

where AW = output-span correcting coefficient.

Figure 6:
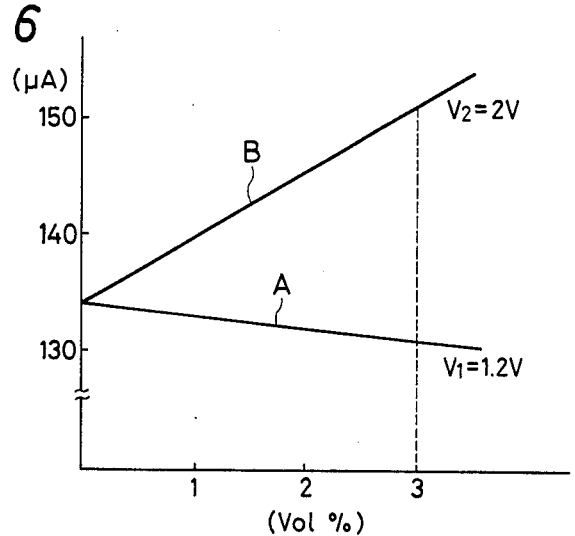
FIG. 6 is a graph showing the relationships between the output current and water vapor content with reference to the applied voltage in the sensor of FIG. 2.

FIG. 6 is a graph showing the relationship between the output current and the water vapor content for the sensor of FIG. 5, wherein the line A represents the relation of the output current to the percent of water vapor in the air when the first voltage $V_1$ is set smaller than a theoretical water decomposition voltage (of about 1.23 V), e.g., at 1.2 V, whereas the line B indicates the relation of the output current to the percent of water vapor when the second voltage $V_2$ is set greater than the theoretical water decomposition voltage (of about 1.23 V).

As set forth above, the voltage applied is divided into two parts: a first voltage that is smaller than the theoretical water decomposition voltage of about 1.23 V with the limited current relying on oxygen only and a second voltage that is greater than the theoretical water decomposition voltage (about 1.23 V) with the limited current relying on oxygen and water vapor, whereby they are switched and applied alternately across the electrodes. The problems inherent in the prior art are thus effectively solved by providing the operational circuit for holding and computing the outputs resulting from the first and second voltages to detect the dry-gas-based or dry-gas-based and humid-gas-based oxygen content with ease. In addition, the effects of the present invention include nullifying the trouble of supplying gas free from water vapor or measuring the water vapor separately for correction purposes, making the sensor not only simple in construction but also compact and easy to operate.

Figure 7:
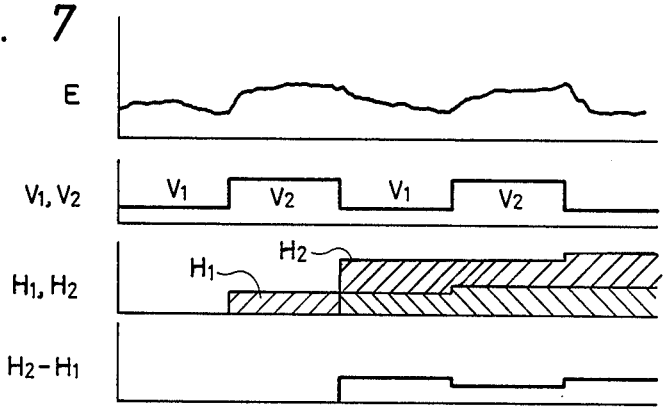
FIG. 7 is an illustration of the function of the sensor of FIG. 5.

As shown in FIG. 7, given input holding values at the time of the first and second voltages $V_1$, $V_2$ in reference to the input signal E are $H_1$, $H_2$, respectively, an output equivalent to the water vapor content is obtainable from $H_2 - H_1$. In this manner, the water vapor content can be determined.

Referring now to FIGS. 8 through 17, a description will be given of a process for producing a limited current type oxygen sensor using oxygen-ion conducting ceramics. The sensor may be mounted on automobiles, boilers, and the like or as an oxygen deficiency monitor. A quantity 100 by weight of fine particulate material (200 Å in saving particle size) of zirconia ($ZrO_2$) stabilized by 8 mol % yittria ($Y_2O_3$), 80 by weight of an organic solvent, 1 by weight of a dispersant, 0.5 by weight of an anti-foam agent, 17 by weight of a binder, and 9 by weight of a plasticizer were weighed, mixed together in a pot mill, and dispersed for 24 hours to prepare a slurry of zirconia. The slurry was defoamed under decompression before being submitted to a tape casting process.

The doctor blade method was employed for tape casting and the slurry was spread to a thickness of 150 $\mu$m on a carrier tape of polyester, whereby a molded product in the form of a tape was obtained. The tape-like molded product was dried by natural drying, then infrared drying at a fixed speed of temperature rise, peeled off the carrier tape, and cut to form five kinds of green sheets, i.e., sheet 31 of FIG. 8(a), sheet 32 of FIG. 9(a), sheet 33 of FIG. 10(a), sheet 34 of FIG. 11(a), and sheet 46 of FIG. 12(a).

Figure 8A:
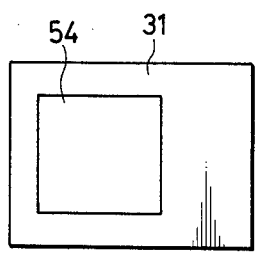
FIGS. 8 (a) and (b) are a top view and side view, respectively, of elements included in the sensor of the present invention.
Figure 8B:
Figure 11A:
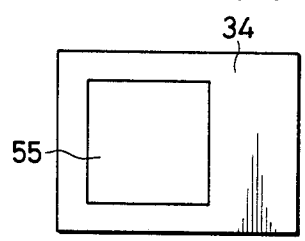
FIGS. 11 (a) and (b) are a top view and side view, respectively, of additional elements of the sensor of the present invention.
Figure 11B:
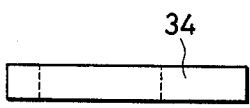
Figure 12A:
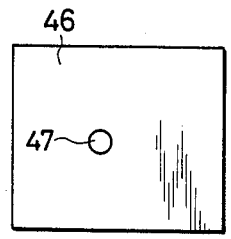
FIGS. 12 (a) and (b) are a top view and side view, respectively, of additional elements of the sensor of the present invention.
Figure 12B:
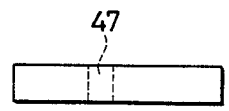

Subsequently, several of the green sheets were subjected to various punching processes. Square holes 54, 55 were punched in the green sheets 31, 34 as shown in FIGS. 8(a) and 11(a), respectively. A window (small through-hole) 47 was punched in the green sheet 46 as shown in FIG. 12(a). There was also prepared a green sheet 46A (not shown with a window 48 smaller in diameter than the window 47).

Figure 9A:
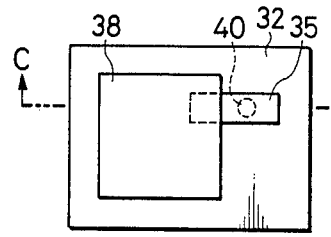
FIGS. 9 (a) and (b) are a top view and sectional view, respectively, of additional elements included in the sensor of the present invention.
Figure 9B:
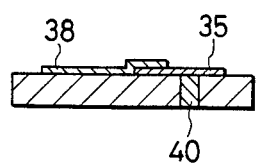
Figure 13:
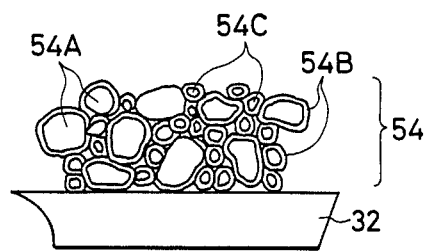
FIG. 13 is an illustration of a mixture of small zirconia particles as sinter-retardant small ceramic grains, a binder and fine platinum particles as fine particles of a precious metal.

Platinum/rhodium alloy paste was used to print a thick film lead 35 having a pattern as shown in FIG. 9(a) on the green sheet 32 and dried. At that time, the inner wall of the through-hole 40 was also plated with the platinum/rhodium alloy paste. An electrode 38 was also printed with the paste in the pattern shown in FIG. 9(a) on the green sheet 32 using a 400-mesh stainless screen. The paste was then dried to obtain the electrode 38. As shown in FIG. 13, a mixture of small zirconia particles 54A stabilized with 8 mol % yttria within the range of 600 Å–900 Å in particle size at the ratio of 92 to 8 by weight was further blended with a binder 54B and a solvent (not shown) at the ratio of 60 to 10 to 30 and dispersed on the sheet 32 to form the electrode 38.

Figure 10A:
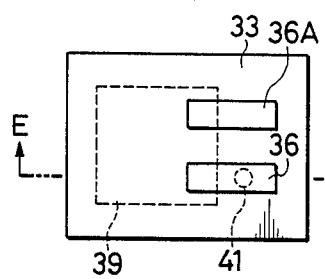
FIGS. 10 (a) and (b) are a top view and sectional view, respectively, of additional elements of the sensor of the present invention.
Figure 10B:
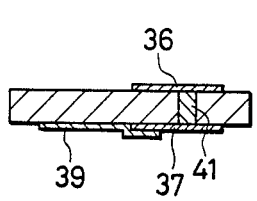

The same kind of platinum/rhodium alloy paste used to print the electrode 38 and lead 35 on the green sheet 32 was used to print thick film leads 36 and 36A on the green sheet 33 as shown in FIG. 10(a). The film leads 36 and 36A were then dried. The inner wall of the through-hole 41 was also printed therewith simultaneously. A thick film lead 37 was printed in the position symmetrical with the thick film lead 36 on the bottom surface of the green sheet 33 and then dried. Further, the same kind of paste used to print the electrode 38 on the green sheet 32 was used to print an electrode 39 having the pattern of FIG. 10(a) on the bottom surface of the green sheet 33. The electrode 39 was then dried.

Figure 14:
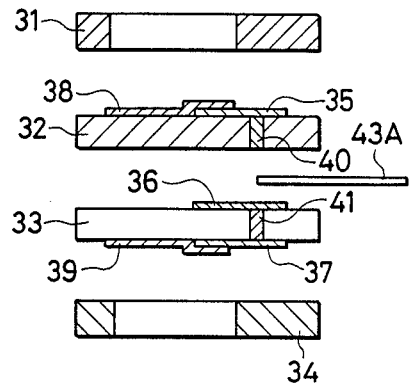
FIG. 14 is an exploded illustration of a green sheet laminate of the sensor of the present invention.
Figure 15A:
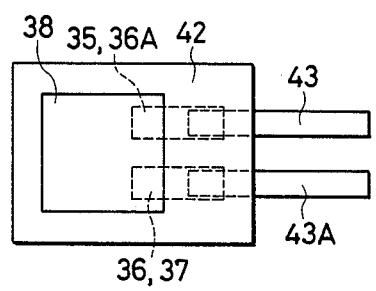
FIGS. 15 (a) and (b) are a top view and a side view, respectively, of a green sheet laminate included in the sensor of the present invention.
Figure 15B:
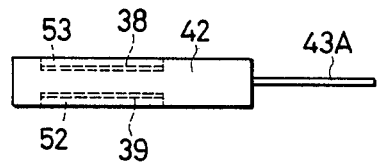

A lamination process then followed. In the lamination process, platinum wires 43, 43A were arranged in the positions shown in FIGS. 14 and 15(a) between the green sheets 32 and 33, which were bonded together by the hot press technique. Subsequently, the green sheets 31 and 34 were arranged above and under the green sheets 32 and 33, respectively, and all of the green sheets 31, 32, 33, and 34 were bonded together by the hot press technique to obtain a laminate 42 shown in FIGS. 15(a) and (b). FIG. 14 shows an exploded view of the lamination structure.

Figure 16A:
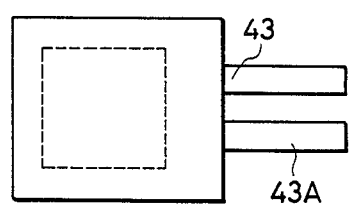
FIGS. 16 (a) and (b) are a top view and a sectional view, respectively, of a ceramic spray-coated oxygen sensor of the present invention.
Figure 16B:
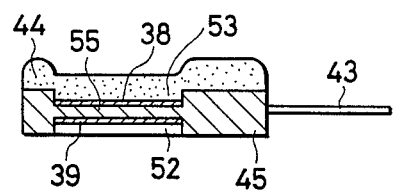

A sintering process was then performed. The laminate 42 of green sheets was heated to 500° C. in air at the rate of 124° C. per hour to burn and oxidize the binder. The laminate 42 was then heated from 500° C. up to 1,500° C. in air at the rate of 250° C. per hour and held for one hour to obtain a sintered compact of zirconia having square grooves 52 and 53 as shown in FIG. 16(b). The electrodes were also formed during this process.

Finally, plasma spray coating was employed to spray ceramic material such as spinel and provide ceramic coating 44 on one side surface of the sintered material to provide an oxygen sensor 45 as shown in FIG. 16(b). The green sheet 46 with the window 47 punched therein as shown in FIGS. 12(a) and (b) and the green sheet 46A (not shown) with the window 48 smaller in diameter than the window 47 were respectively arranged under and above the laminate formed from the green sheets 31, 32, 33, and 34 so that the six green sheets 46A, 31, 32, 33, 34, 46 could be bonded together by the hot press technique. It is also possible to obtain an oxygen sensor 51 having the vacancies 49 and 50 as shown in FIG. 17(b), by sintering the aforesaid laminate.

As set forth above, the oxygen sensor 45 or 51 (FIG. 16(b) FIG. 17(b)) is obtainable through the slurry preparation, tape casting, punching, printing, lamination, and sintering steps.

When the yttria ($Y_2O_3$) stabilized fine zirconia particles of 200 Å in average particle size are heated at 1,500° C. for one hour, they become sintered oxygen ion-conducting ceramics. The platinum/rhodium alloy used as a thick film lead is excellent in heat resistance as it contains rhodium and, when sintered at 1,500° C., becomes a thick film lead provided with good electrical conductivity.

The electrode paste contains the binder 54B and the small zirconia particles 54A of 600 Å to 900 Å in particle size in addition to the fine platinum particles 54C of 100 Å to 200 Å in particle size which adhere to each other while being encapsulated by the binder 54B. If the mixture 54 is calcined, the binder will burn and volatilize, leaving the small grained zirconia and smaller grained platinum. The zirconia particles have a particle size of as large as 600 Å–900 Å, are hard to sinter by themselves, and work as a sinter-preventive agent against the fine platinum particles. Consequently, the fine-grained platinum will be calcined while maintaining the porous state without sintering if the mixture 54 is calcined at 1,500° C. which is the same temperature as that at which the fine-grained zirconia (200 Å average in size) intended for the oxygen-ion conducting ceramic thin plate and an electrode active electrochemically as well as conductive electrically can be formed.

Since both the processing steps of sintering the oxygen-ion conducting ceramics and forming the electrodes can be conducted simultaneously at the same temperature, these two steps can be combined. Production costs are thus reduced in comparison with the conventional process requiring two steps.

The operation of the oxygen sensor will subsequently be described. In the oxygen sensor 45 of FIGS. 16(a) and (b), a constant potential is applied across the electrodes 38 and 39, which operate as the cathode and anode, respectively. The ceramic coating 44 is provided in the form of a porous thick film of, for example, spinel which restricts the diffusion of oxygen. The oxygen gas diffuses through the pores of the ceramic coating 44 and reaches the electrode 38 (cathode) where its changes into oxygen ions because of the following reaction (1).

$$O_2 + 4e \rightarrow 2O^2 \qquad (1)$$

Fine precious metal particles such as those of rhodium and iridium other than platinum may be used for the paste for use in printing the electrodes 38 and 39 and fine particles of their alloys are also usuable. As a sinter-preventive agent, ceramics relatively sinter-retardant against the oxygen-ion conducting ceramics 600 Å to 900 Å; in particle size, e.g., alumina ($Al_2O_3$) and thoria ($ThO_2$), may be utilized in proper particle sizes.

Since the fine precious metal particles mixed with the small ceramic particles that are relatively sinter-retardant are calcined to form the electrodes, the sintering of the fine precious metal particles are suppressed and the calcined electrodes remain porous, even at temperatures at which the oxygen-ion conducting ceramics are sintered because of the sinter-preventive action of the small grained ceramics. Electrodes having good electrochemical properties are formed, whereby the sintering of the oxygen-ion conducting ceramics and the calcination of the electrodes can be carried out in one step instead of two. The process of producing the sensor is simplified and shortened.

Moreover, as the result of the fine precious metal particles being mixed with the small ceramic sinter-retardant particles and calcined to form the electrodes, the sintering of the oxygen-ion conducting ceramics, and the calcination of the electrodes being carried out in one step, it becomes possible to provide the electrodes on the inside of the oxygen-ion conducting ceramics.

This increases the flexibility in the construction of the oxygen sensor.

Figure 19:
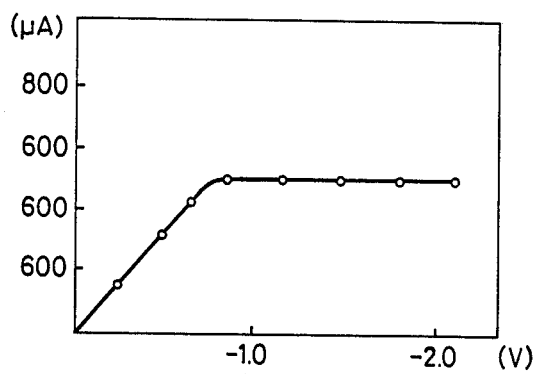
FIG. 19 is a graph showing the current-voltage characteristics of the oxygen sensor according to the embodiment of FIGS. 18 (a) and (b)

Another embodiment of the present invention is shown in FIGS. 18(a) and (b). A small oxygen diffusion orifice 81A allows the desired amount of diffusion oxygen to be available by properly selecting the dimensions of a pattern being printed when the combustible paste is applied. The orifice 81A may be a square 25 $\mu$m height, 150 $\mu$m in width, and 1 mm in length. If the oxygen ion current as the output signal of the oxygen sensor is measured in air as the output signal (at a partial oxygen pressure of 0.21), the characteristics of FIG. 19 are attained at a temperature of 400° C. A plateau current of about 500 $\mu$A is obtained in the neighborhood of $-1.0$ V as the potential of the cathode. This demonstrates that the oxygen sensor of the present invention can be operated at relatively low temperatures.

A space 77 (FIG. 18(b)) about 0.1 mm high can be readily formed by properly selecting the thickness of a second green sheet 61D (FIG. 20) to compensate for changes in thickness during sintering of the plate. The response speed of the oxygen sensor can be increased by setting the area of each electrode at, e.g., 4 mm$^2$, to enable the internal volume of the space 77 to be made small. The thermal efficiency is also improved by decreasing the height of the space 77.

Electrode paste is printed, dried and calcined to obtain the cathode 70 and anode 71, each of which contains small grained zirconia. The fine platinum particles can be calcined together with the green sheet 61E of small grained zirconia because the fine platinum particles are prevented from sintering by the small grained zirconia. A cover 78 (see FIG. 20) can be incorporated as a laminated electrolytic thin zirconia plate 79 (FIG. 18(b)). Since the size (600 Å 900 Å) of the small zirconia particles contained in the electrode paste is greater than the size (100 Å to approximately 200 Å) of the fine platinum particles constituting the green sheets, the zirconia particles are not appreciably sintered at 1,450° C. where the platinum particles would be sintered if it wasn't for the pressure of the zirconia particles. A porous electrode is consequently formed, making it possible to integrate the elements of the cover 78 (see FIG. 20) into the solid electrolyte thin zirconia plate 79 and to form the electrodes 70 and 71 having excellent properties.

When the green sheets that comprise the solid electrolyte thin zirconia plate 79 are formed and sintered as described above, an extremely thin plate about 100 $\mu$m in thickness can be formed. Because the thickness of the solid electrolytic thin zirconia plate 79 is reduced, the electrical resistance thereof is reduced. Consequently, the oxygen sensor can be operated at a low temperature of roughly 400° C.

Figure 21:
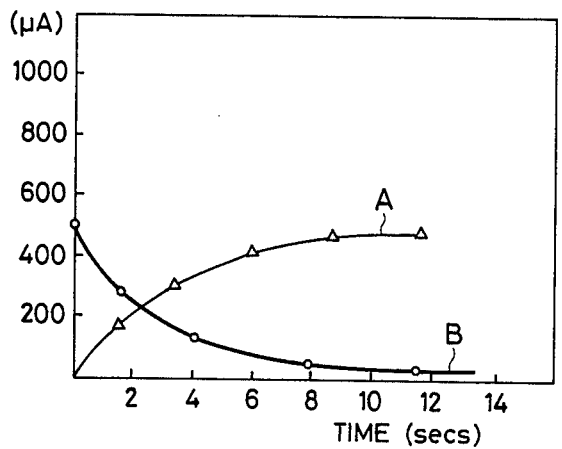
FIG. 21 is a graph showing the response characteristics of the oxygen sensor of FIGS. 18(a) and (b)
Figure 22:
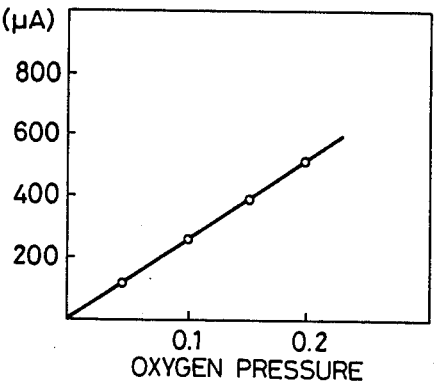
FIG. 22 is a graph showing a calibration curve pertaining to the oxygen sensor of FIGS. 18(a) and (b)

The response characteristics of the oxygen sensor thus prepared shows a response of 90% in 10 seconds or less at 400° C. when nitrogen (partial oxygen pressure=0) is substituted for air at a partial oxygen pressure of 0.21 (FIG. 21, curve A) and when air is substituted for nitrogen (FIG. 21, curve B). FIG. 22 illustrates a calibration curve at a set potential of $-1.0$ V and a temperature of 400° C.

As shown in FIG. 18(b), when the cover 78 (see FIG. 20) is formed from solid zirconia electrolyte and incorporated as the solid electrolytic thin zirconia plate 79, there remain no distinctive boundaries as in the case where the elements of the cover are separately formed and laminated together. Accordingly, sudden changes in temperature at the time the oxygen sensor is started will not damage the cover and the reliability of the sensor is thus improved. Moreover, the adoption of the above integrated construction has several inherent advantages over the process of manufacturing oxygen sensors wherein minute structures are separately fabricated and then joined.

As shown in FIG. 18(b), a heater 62 is embedded in the plate 79 and the heat generated thereby is not radiated from the sensor because the zirconia is a poor conductor of heat. Thus, by burying the heater 62 in the solid electrolyte zirconia 79, unwanted uninvited radiation of heat decreases, and the heater 62 more effectively heats the oxygen sensor at a lower power level. In the case of a 4 mm$\times$5 mm sensor, for instance, a sensor temperature of 400° C. can be obtained at 1 W. Moreover, assuming that a platinum/rhodium alloy heater is buried in the solid zirconia electrolyte, evaporation of the heater component does not occur during heater operation. Consequently, the heater will not become thinner as it is used, is less likely to break, and will have its life prolonged. If the heater is arranged apart from the cathode 70 or anode 71 the heater current and signal current (oxygen-ion current flowing across the cathode and anode electrodes) are kept free from interference with each other.

Another embodiment of the present invention is shown in FIGS. 23(a) and (b) where there is provided a space 217 (preferably square in shape) within the oxygen-ion conductor of the oxygen sensor and an orifice 221A for oxygen diffusion which communicates with the space 217. A heater 202, such as an M-shaped heater, for heating a detection wall 219, i.e., the portion between the cathode 210B and the anode 211B, of the oxygen-ion sensor. A portion of the detection wall 219 contacts the side plane 222 of the space 217. The cathode electrode 210B is exposed to the space 217 and its peripheral edge is buried in the sensor proper at the side of the space. The buried portion of the cathode is arranged opposite to the outer peripheral plane of the heater 202. The anode 211B is preferably the same size as the cathode 210B and has a surface exposed to the exterior of the sensor.

The heat from the heater 202 flows to the cathode 210B across the space 217 and via the side plane 222 thereof. The space 217 provides high resistance to thermal conduction because of poor thermal conduction through air. On the other hand, the portion of the detection wall 219 forming the wall portion 222 is composed of an oxygen-ion conductor and has a thermal conductivity greater than that of air. Since the outer periphery of the heater 202 is not separated from the buried peripheral edge of the cathode 210B by the space 217, the temperature of the buried peripheral edge of the cathode 210B is higher than the portion of the cathode electrode 210B exposed to the space 217. Since the material in which the cathode 210B is buried is porous as aforesaid, the electrode 210B as a whole is operated at a high mean temperature. It is, therefore, possible to reduce the power required for the heater 202 and the life of the heater can effectively be prolonged.

FIG. 24 shows electric characteristics of a conventional oxygen sensor (solid line - electrode 2.0 mm$\times$2.0 mm) and of a sensor according to the present invention (dotted line-electrode 2.3 mm$\times$2.3 mm) with heater power as a parameter. The electric characteristics represent the relation of the cathode potentials with respect to the anode electrode and the oxygen-ion current (the current resulting from the reduction of the oxygen diffusion) flowing through the oxygen-ion conductor across both the electrodes. The appearance of plateaus designates that the oxygen gas diffused through the orifice 221A for oxygen diffusion that has totally been converted into current.

With the same heater power used for comparison, the sensor according to the present invention reaches the plateau area at a lower potential and this means that the mean electrode temperature according to the present invention is higher at the same level of heater power. Since the heater is more effective, the heater power may be reduced.

If the portion of the cathode 210B exposed to the space 217 exhibits reduced conductivity because of stress incurred at the time of hot press forming, the reduced conductivity will not spread to the whole area. The influence of the reduced conductivity in the cathode 210B is compensated for by burying the peripheral edge of the cathode 210B in the oxygen-ion conductor.

The oxygen sensor according to the present invention includes a sensor body arranged to enclose the space into which the gas being examined (included oxygen) is introduced and has a gas detection wall formed by an oxygen-ion conductor. The gas diffusion anode is provided on the outer face of the detection wall of the sensor body. The gas diffusion cathode is provided on the detection wall of the sensor body, with its peripheral edge buried in the side of the sensor body in contact with the gas detection face. The heating means is arranged in a portion of the sensor body other than the wall so as to indirectly heat the detection wall thereof. The buried peripheral edge of the cathode is subject to heat from the heater conducted through an oxygen-ion conductor and causes the cathode to operate at a higher mean temperature as a whole. Consequently, the power required for the heater is reduced, the heater life is extended, and the reliability of the oxygen sensor is improved.

Figure 25A:
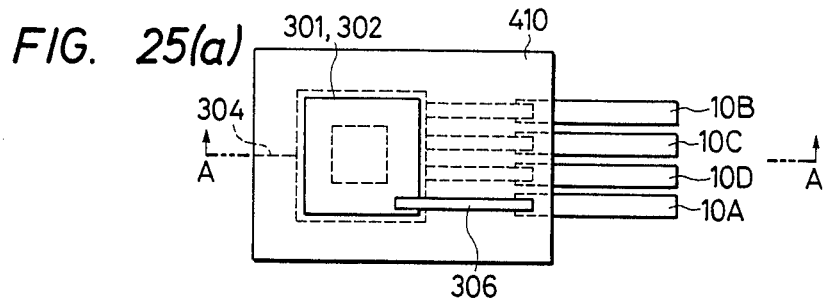
FIGS. 25 (a) and (b) are a top view and a sectional view, respectively, of a sixth embodiment of the oxygen sensor according to the present invention.
Figure 25B:
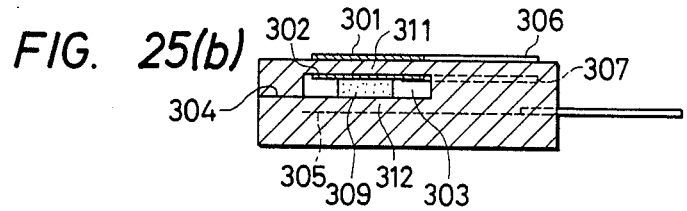

FIGS. 25(a) and (b) illustrate another embodiment of the oxygen sensor of the present invention. The oxygen sensor according to this embodiment is designed to reduce the power required by the heater by minimizing heat resistance between the heater and the detection means, to decrease thermal distortion within the sensor, to stabilize characteristics of the sensor, to attain higher reliability, and to facilitate ease of production.

The method of producing an oxygen sensor 410 according to this embodiment comprises printing electrodes 301, 302, a heater 305, and leads 306, 307 by screen printing on green sheets of solid electrolytic zirconia, joining the green sheets under pressure using the hot press method, and sintering the combination. A detection means 311 is formed on the outer side of the electrode 301 and the electrodes 301, 302 are installed opposite to each other on a wall 311 of a space 303 that communicates with an orifice 304 for restricting oxygen diffusion. A heater 305 is embedded in the sensor at a distance from the space 303 approximately equal to the thickness of the wall portion 311. A heat transmitting element 309 is provided in the space 303 in contact with the wall portion 311. The heat transmitting element 309 is provided roughly in the center of the space 303 in such a manner as to thermally couple the wall portion 311 with a second wall portion 312 separating the heater 305 from the space 303. The heat transmitting element 309 may be formed from a small piece cut out of a green sheet similar to those laminated and bonded together with the hot press method as aforesaid. The heat transmitting element 309 is set in position within the space 303 and is joined in the sensor during the hot press process.

Figure 26:
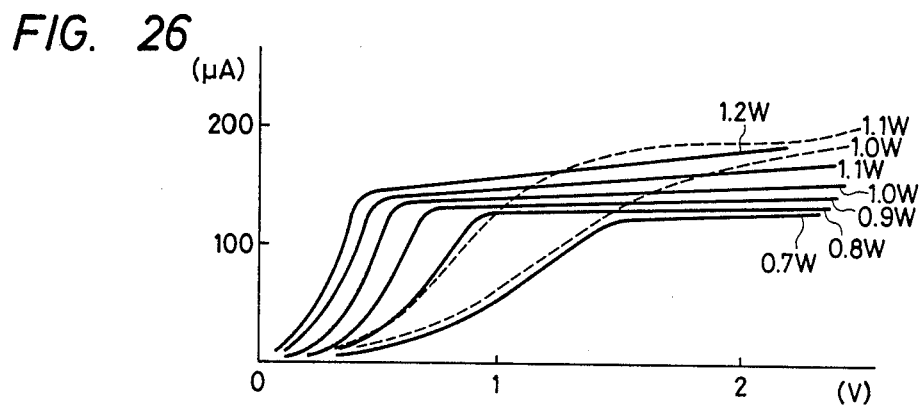
FIG. 26 is a graph showing comparisons in characteristics between a conventional oxygen sensor and an oxygen sensor of the present invention.

FIG. 26 shows characteristics of the oxygen sensor of FIGS. 25(a) and (b). The continuous lines show a sensor wherein a $1.1 \times 1.1$ mm$^2$ heat transmitting element 309 is formed mm$^2$ space 303. The dashed line corresponds to a substantially identical sensor without the heat transmitting element 309. As was the case illustrated in FIG. 24, the sensor of FIGS. 25(a) and (b) reaches the plateau area at a significantly lower potential than a sensor not including the element 309. Moreover, at potentials over 2 V the power level of the sensor of FIGS. 25(a) and (b) can be reduced by about 30% and still perform as effectively as prior art sensors.

When power 1.5 times greater than the rated power is applied to drive the system, the rate of defects in airtightness remains zero with a sensor including the heat conducting means 309 in comparison with about 10% thereof without the formation of the means 309. Accordingly, it is readily understood that the characteristic curves shown by the continuous line afford abundant evidence of reduction in thermal distortion.

Since a green sheet for use in forming the heat conducting means 309 has already been installed within the space 303 when the green sheets are joined together under pressure with the hot press and sintered, any deformation on the periphery of the space 303 can be suppressed even during the process where pressure and heat are applied.

Figure 27A:
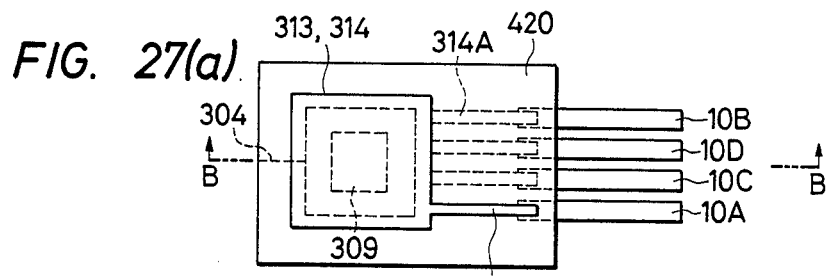
FIGS. 27 (a) and (b) are a top view and a sectional view respectively, of a seventh embodiment of an oxygen sensor according to the present invention.
Figure 27B:
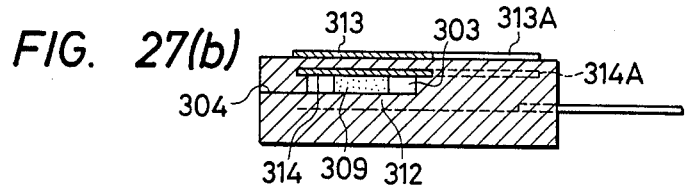

FIGS. 27(a) and (b) are schematic structural views of still another embodiment of the present invention wherein like reference numerals are given to those elements having like functions to eliminate previous description. An oxygen sensor 420 incorporates electrodes 313, 314 and leads 313A, 314A, using the same material under the same process. The oxygen sensor 420 includes a small piece of green sheet cut to size as a heat transmitting element 309 bonded within a space 303 when the green sheets are laminated by the hot press technique.

As set forth above, the problems inherent in the prior art are satisfactorily solved since the heat deriving from the heater is directly conducted to the center of the electrode through the heat transmitting element and the thermal resistance between the heater and the heat transmitting element is reduced and the heater temperature can be set lower as the detection means is effectively heated. The life of the heater is thereby prolonged and, because the difference in temperature between the heater and other portion of the sensor decreases, the sensor will be free from thermal distortion, less likely to be damaged, and less subject to characteristic fluctuation.

Moreover, since the green sheet for use as a heat transmitting element is bonded when the green sheets are joined under pressure with the hot press and sintered, deformation is prevented from occuring particularly in the space and its surroundings during those processing steps and oxygen sensor production yield is effectively improved.

Although it has been so arranged that the heat transmitting element in the aforesaid embodiments are composed of the same material as that used to prepare solid electrolytes in the other portions, the present invention is not limited to such arrangements. Any electrically insulating material may be used that is similar in linear expansion coefficient and has a high thermal conductivity.

What is claimed is:

1. A limited current type oxygen sensor comprising:
   an oxygen-ion conducting solid electrolyte element, said element having a top surface and a bottom surface;
   a first electrode on said bottom surface;
   a second electrode on said top surface;
   means for covering said second electrode, said covering means including at least one diffusion orifice permitting ambient gas to diffuse therethrough toward said second electrode;
   means for alternately applying a first voltage to one of said electrodes and for measuring a level of a first current flowing through said element between said first electrode and said second electrode responsive to the application of said first voltage and a second voltage different from said first voltage to said one electrode and for measuring a level of a second current flowing through said element between said first electrode and said second electrode responsive to the application of said second voltage, said first voltage having a level less than the theoretical water decomposition voltage such that said first current corresponds to the decomposition of oxygen on said surface of said second electrode and said second voltage having a level greater than the theoretical water decomposition voltage such that said second current corresponds to the decomposition of oxygen and water vapor on said surface of said second electrode; and
   operational circuit means receiving said first current and said second current and for determining therefrom the dry-gas-based and humid-gas-based oxygen content of said ambient gas.

2. A limited current type oxygen sensor according to claim 1, wherein said solid electrolyte element comprises yittria-stabilized zirconia.

3. A limited current type oxygen sensor according to claim 2, wherein said first electrode and said second electrode are formed from a calcined mixture of precious metal grains of a particle size of 100 Å to 200 Å and ceramic grains of a particle size of 600 Å to 900 Å, said ceramic grains selected from the group consisting of yittria-stabilized zirconia ($ZrO_2$-$Y_2O_3$), alumina ($Al_2O_3$) and thoria ($ThO_2$).

4. A limited current type oxygen sensor according to claim 3, wherein said precious metal grains are made of platinum.

5. A limited current type oxygen sensor according to claim 1, wherein said oxygen sensor further comprises a space disposed between said second electrode and a portion of said covering means, said at least one diffusion orifice thereof communicating to said space.

6. A limited current type oxygen sensor according to claim 5, wherein said solid electrolyte element comprises yittria-stabilized zirconia.

7. A limited current type oxygen sensor comprising:
   an oxygen-ion conducting solid electrolyte element, said element having a top portion and a bottom portion, said top portion having a bottom surface and said bottom portion having a top surface in opposition to said bottom surface of said top portion and a bottom surface, a portion of said bottom surface of said top portion being separated from said top surface of said bottom portion to define a space therebetween, said element including a diffusion orifice permitting ambient gas to enter said space;
   a first electrode formed on said bottom surface of said bottom portion;
   a second electrode on said top surface of said bottom portion, a portion of said second electrode communicating with said space;
   a heater buried in said top portion of said element;
   means for supplying current to said heater to generate heat for heating said space;
   means for alternately applying a first voltage to one of said electrodes and for measuring a level of a first current flowing through said bottom portion of said element between said first electrode and said second electrode responsive to the application of said first voltage and a second voltage different from said first voltage to said one electrode and for measuring a level of a second current flowing through said element between said first electrode and said second electrode responsive to the application of said second voltage, said first voltage having a level less than the theoretical water decomposition voltage such that said first current corresponds to the decomposition of oxygen in said space and said second voltage having a level greater than the theoretical water decomposition voltage such that said second current corresponds to the decomposition of oxygen and water vapor in said space; and
   operational circuit means receiving said first current and said second current and for determining therefrom a dry-gas-based and humid-gas-based oxygen content of said ambient gas.

8. A limited current type oxygen sensor according to claim 7, wherein said solid electrolyte element comprises yittria-stabilized zirconia.

9. A limited current type oxygen sensor according to claim 8, wherein said heater is formed of a platinum/rhodium alloy.

10. A limited current type oxygen sensor according to claim 9, wherein said electrodes are formed of a calcined mixture of precious metal grains of a particle size of 100 Å to 200 Å mixed with ceramic grains of a particle size of 600 Å to 900 Å selected from the group consisting of yittria-stabilized zirconia ($ZrO_2$-$Y_2O_3$), alumina ($Al_2O_3$) and thoria ($ThO_2$).

11. A limited current type oxygen sensor according to claim 10, wherein said precious metal grains are formed of platinum.

12. A limited current type oxygen sensor according to claim 11, wherein a portion of said second electrode is buried in said solid electrolyte element.

13. A limited current type oxygen sensor according to claim 12, wherein said heater is buried in said top portion of said element and is separated from said space by a distance approximately equal to the thickness of said bottom portion of said element separating said first electrode and said second electrode.

14. A limited current type oxygen sensor according to claim 12, further including a heat transmitting element provided in said space and being in contact with said bottom surface of said top portion and said second electrode.

* * * * *